United States Patent [19]

Klaus et al.

[11] Patent Number: 4,992,574

[45] Date of Patent: Feb. 12, 1991

[54] BENZOCYCLOHEPTENE DERIVATIVES

[75] Inventors: Michael Klaus, Weil am Rhein, Fed. Rep. of Germany; Peter Mohr, Basel, Switzerland

[73] Assignee: Hoffmann-La Roche Inc., Nutley, N.J.

[21] Appl. No.: 263,651

[22] Filed: Oct. 27, 1988

[30] Foreign Application Priority Data

Nov. 6, 1987 [CH] Switzerland .......................... 4346/87
Aug. 10, 1988 [CH] Switzerland .......................... 3018/88

[51] Int. Cl.$^5$ ............................................ C07C 69/76
[52] U.S. Cl. .......................................... 560/8; 560/51; 560/56; 562/462; 562/466; 562/473; 562/474; 564/169; 564/172; 564/180; 514/544; 514/569; 514/617; 514/621
[58] Field of Search ............... 560/8, 51, 56; 562/462, 562/466, 473, 474; 564/169, 172, 180; 514/544, 569, 617, 621

[56] References Cited

U.S. PATENT DOCUMENTS

| | | | |
|---|---|---|---|
| 4,326,055 | 4/1982 | Loeliger | 560/51 |
| 4,714,786 | 12/1987 | Wuesi et al. | 560/56 |
| 4,870,219 | 9/1989 | Klaus et al. | 560/51 |

FOREIGN PATENT DOCUMENTS 2190378A 11/1987 Fed. Rep. of Germany .

Primary Examiner—Paul J. Killos
Attorney, Agent, or Firm—George M. Gould; Bernard S. Leon; William G. Isgro

[57] ABSTRACT

A compound of the formula

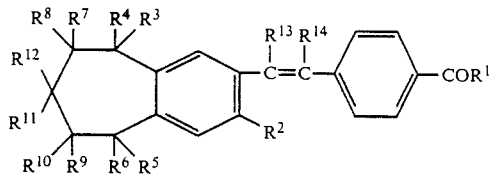

wherein
$R^1$ is hydroxy, lower-alkoxy, amino, mono- or di-lower-alkylamino;
$R^2$ is hydrogen, alkyl, akoxy or halogen;
$R^3$, $R^4$, $R^5$, $R^6$, $R^{11}$ and $R^{12}$ independently are hydrogen or lower-alkyl;
$R^3$ and $R^5$ taken together are methylene or hydroxymethylene;
$R^7$, $R^8$, $R^9$ and $R^{10}$ independently are hydrogen or lower-alkyl;
$R^{11}$ and $R^{12}$ taken together are oxo or spiro-cyclo-lower alkyl; or $R^{11}$ is hydrogen and $R^{12}$ is hydroxy or acetoxy; and one of the residues $R^{13}$ and $R^{14}$ is hydrogen and the other is lower-alkyl or trifluoromethyl, as well as physiologically compatible salts of carboxylic acids of formula I, which can be used as medicaments, especially for the treatment of neoplasms, acne and psoriasis, are described. The compounds of the invention can be prepared by the synthesis of the $C(R^{13})=C(R^{14})$ double bond according to Wittig from a corresponding bicyclic component and a corresponding monocyclic component and optional subsequent transformation of functional groups.

22 Claims, No Drawings

BENZOCYCLOHEPTENE DERIVATIVES

BRIEF DESCRIPTION OF THE INVENTION

The invention relates to benzocycloheptene derivatives, their preparation and pharmaceutical preparations which contain these compounds. The benzocycloheptene derivatives in accordance with the invention are compounds of the formula $$\text{Structure I}$$

wherein
$R^1$ is hydroxy, lower-alkoxy, amino, mono- or di-lower-alkylamino;
$R^2$ is hydrogen, alkyl, alkoxy or halogen;
$R^3$, $R^4$, $R^5$, $R^6$, $R^{11}$ and $R^{12}$ independently are hydrogen or lower-alkyl;
$R^3$ and $R^5$ taken together are metheylene or hydroxymethylene;
$R^7$, $R^8$, $R^9$ and $R^{10}$ independently are hydrogen or lower-alkyl;
$R^{11}$ and $R^{12}$ taken together are oxo or spiro-cyclo-lower alkyl; or $R^{11}$ is hydrogen and $R^{12}$ is hydroxy or acetoxy; and one of the residues $R^{13}$ and $R^{14}$ is hydrogen and the other is lower-alkyl or trifluoromethyl, as well as physiologically compatible salts of carboxylic acids of formula I.

The compounds of formula I have anti-seborrheic, anti-keratinizing, anti-neoplastic and anti-allergic/anti-inflammatory activity and are therefore useful as anti-seborrheic, anti-keratinizing, anti-neoplastic and anti-allergic/anti-inflammatory agents.

DETAILED DESCRIPTION OF THE INVENTION

The benzocycloheptene derivatives of the invention are compounds of the formula $$\text{Structure I}$$

wherein
$R^1$ is hydroxy, lower-alkoxy, amino, mono- or di-lower-alkylamino;
$R^2$ is hydrogen, alkyl, alkoxy or halogen;
$R^3$, $R^4$, $R^5$, $R^6$, $R^{11}$ and $R^{12}$ independently are hydrogen or lower-alkyl;
$R^3$ and $R^5$ taken together are methylene or hydroxymethylene;
$R^7$, $R^8$, $R^9$ and $R^{10}$ independently are hydrogen or lower-alkyl;
$R^{11}$ and $R^{12}$ taken together are oxo or spiro-cyclo-lower alkyl; or $R^{11}$ is hydrogen and $R^{12}$ is hydroxy or acetoxy; and one of the residues $R^{13}$ and $R^{14}$ is hydrogen and the other is lower-alkyl or trifluoromethyl, as well as physiologically compatible salts of carboxylic acids of formula I, that is, the compounds of formula I wherein $R^1$ is hydroxy.

A preferred group of compounds of formula I of the invention are those in which $R^1$ is hydroxy, lower-alkoxy, amino, mono- or di-lower-alkylamino; $R^2$ is hydrogen, alkyl, alkoxy or halogen; $R^3$, $R^4$, $R^5$, $R^6$, and independently are hydrogen or lower-alkyl; $R^3$ and $R^5$ taken together are methylene; $R^7$, $R^8$, $R^9$ and $R^{10}$ independently are hydrogen or lower-alkyl; $R^{11}$ and $R^{12}$ taken together are oxo or $R^{11}$ is hydrogen an is hydroxy; and one of the residues $R^{13}$ and $R^{14}$ is hydrogen and the other is lower-alkyl or trifluoromethyl, and, when $R^1$ is hydroxy, physiologically compatible salts thereof. Furthermore, compounds of formula I in which $R^1$ is hydroxy or lower-alkoxy and those in which $R^2$ is hydrogen, and $R^3$-$R^{12}$ are hydrogen or lower-alkyl are preferred.

Other preferred compounds of formula I are those in which at least one of the residues $R^3$-$R^{12}$ is lower--alkyl; those in which $R^{11}$ and $R^{12}$ taken together are oxo; those in which $R^{11}$ is hydrogen and $R^{12}$ is hydroxy; and those in which $R^3$ and $R^5$ taken together are methylene. Ethyl p-[(E)-2-(6,7,8,9-tetrahydro-7,7-dimethyl-5H-benzocyclohepten-2-yl)-propenyl]benzoate is of particular interest.

As used herein, the term "lower" denotes groups with 1-6 C-atoms. Alkyl and alkoxy groups can be straight-chain or branched, for example, methyl, ethyl, propyl, isopropyl, butyl, sec.-butyl and the like, methoxy, ethoxy, propoxy, isopropoxy, butoxy, sec.-butoxy and the like. Alkyl and alkoxy groups as $R^2$ preferably contain up to 10 C-atoms, for example, methyl, ethyl, propyl, butyl, octyl, nonyl, decyl and the like, and methoxy, ethoxy, propoxy, butoxy, octyloxy, nonyloxy, decyloxy and the like. Halogen denotes fluorine, chlorine, bromine and iodine.

Examples of physiologically compatible, or pharmaceutically acceptable, salts of the carboxylic acids of formula I are alkali salts such as the sodium and the potassium salts, alkaline earth metal salts such as the calcium salts and substituted and unsubstituted ammonium salts.

The compounds of formula I can exist as trans or cis isomers or cis/trans isomeric mixtures. In general, the trans compounds of formula I are preferred.

The compounds of formula I and their salts can be prepared in accordance with the invention by reacting a compound of the formula $$\text{Structure II}$$

with a compound of the formula $$\text{Structure III}$$

wherein A is the residue —CH(R¹³)P+(Q)₃Y and B is the residue —CO(R¹⁴)—; or A is the residue —CO(R¹³)— and B is the residue —CH₂—PO(OAlk)₂; Q is aryl, Y is the anion of an organic or inorganic acid, Alk is lower alkyl group and R¹-R¹⁴ are as previously described and wherein a hydroxy or oxo group present as or R¹² or R¹¹ and R¹² is present in protected form, cleaving off from the condensation product a hydroxy or oxo protecting group which may be present and, if desired, saponifying an ester group —COR¹ of the thus-obtained compound of formula I or converting it into a carboxamino group or a N-mono- or dialkylated carboxamino group.

The reaction of the compounds of formulas II and III can be carried out according to the known methods of the Wittig or Horner reaction.

In the case of the Wittig reaction, that is, using a compound of formula II wherein A=—CH(R¹³)P+(Q)₃Y⁻ or of formula III wherein B=—CH(R¹⁴)P+(Q)₃Y⁻, the reactants are reacted with one another in the presence of an acid-binding agent, for example, in the presence of a strong base such as for example, butyllithium, sodium hydride or the sodium salt of dimethyl sulfoxide, but especially in the presence of an ethylene oxide which is optionally substituted by lower alkyl such as 1,2-butylene oxide, optionally in a solvent, for example in an ether such as diethyl ether or tetrahydrofuran or in an aromatic hydrocarbon, such as, benzene, at a temperature range lying between room temperature and the boiling point of the reaction mixture.

Of the inorganic acid anions Y⁻, the chloride and bromide ion or the hydrosulfate ion are preferred and of the organic acid anions the tosyloxy ion is preferred. The aryl residue Q is preferably a phenyl residue or a substituted phenyl residue, for example a lower-alkyphenyl residue such as p-tolyl.

In the case of the Horner reaction, that is, using a compound of formula II wherein A=—CH(R¹³)—P(O)(OAlk)₂ or of formula III wherein B=—CH(R¹⁴)—P(O)(OAlk)₂, the reactants are condensed with the aid of a base and preferably in the presence of an inert organic solvent, for example, with the aid of sodium hydride in benzene, toluene, dimethylformamide, dimethyl sulfoxide, tetrahydrofuran, dioxane or 1,2-dimethoxyethane, or also with the aid of an alcoholate in an alkanol, for example, potassium t-butylate in t-butanol or sodium methylate in methanol, at a temperature range lying between 0° and the boiling point of the reaction mixture.

The alkoxy residues OAlk are preferably lower alkoxy residues with 1-6 carbon atoms such as methoxy, ethoxy or propoxy.

A carboxylic acid ester of formula I can be hydrolyzed to a carboxylic acid of formula I in a known manner, for example, by treatment with alkalis, especially by treatment with aqueous alcoholic sodium hydroxide solution or potassium hydroxide solution at a temperature range lying between room temperature and the boiling point of the reaction mixture.

A carboxylic acid of formula I can be converted in a known manner, for example, by treatment with thionyl chloride, preferably in pyridine, or phosphorus trichloride in toluene or oxalyl chloride in dimethylformamide/benzene, into the acid chloride which can then be converted by reaction with alcohols into esters and with amines into the corresponding amides. Amides can also be obtained directly from carboxylic acid esters of formula I. for example, by treatment with lithium amide. The lithium amide is preferably reacted with the relevant ester at room temperature. Carboxylic acid amides of formula I can be mono- or di-alkylated in a known manner. for example, by treatment with alkyl halides in the presence of a base, whereby this reaction for the preparation of compounds of formula I in which R¹¹ and R¹² are oxo is conveniently carried out prior to the cleavage of the oxo protecting group.

The compounds of formula I can be present in the trans or cis form. In the process described above, they are obtained for the most part in the trans form. Cis components which may be obtained can be separated, when desired, in a known manner or can be isomerized to the trans isomers, for example, by acid catalysis or photochemically.

The starting compounds of formulas II and III, insofar as their preparation is not known or is not described hereinafter, can be prepared in analogy to known methods or to the methods described hereinafter.

A compound of the formula

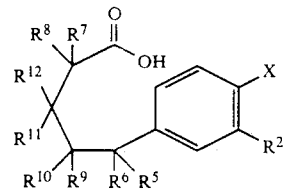

wherein R² and R⁵-R¹² are as previously described and X is hydrogen or bromine,
can be cyclized to a compound of the formula

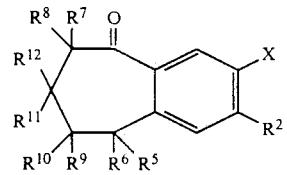

by treatment with acids such as polyphosphoric acid or by conversion into the acid chloride and subsequent treatment with a Friedel-Crafts catalyst. The oxo group in the compound of formula V can then be removed by treatment with reducing agents, whereby there is obtained a compound corresponding to formula II in which A represents hydrogen or a bromine atom. After conversion into a Grignard compound, the bromo compound can be converted with an aldehyde R¹³-CHO into the corresponding benzyl alcohol of the formula

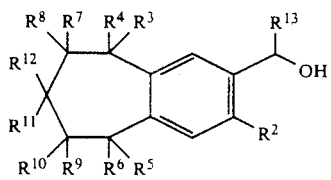

A compound of formula X can then be converted via the corresponding benzyl halide into a phosphonium salt, that is, a compound of formula II in which A is the residue —CH(R¹³)P+(Q)₃Y⁻. Alternatively, the compound of formula X can be oxidized by means of oxidizing agents such as manganese dioxide to the ketone, that is, a compound of formula II wherein A=—CO(R¹³).

Reduction products obtained from compounds of formula V wherein X=hydrogen can be converted into compounds of formula II in which A is the residue —CO($R^{13}$) with an acid chloride $R^{13}$COCl in a Friedel-Crafts reaction.

The compounds of formula IV can be prepared by reacting glutaric acid anhydride or a correspondingly substituted derivative thereof according to Friedel-Crafts with benzene or bromobenzene or an o-alkyl, o-alkoxy or o-halo derivative thereof to give a compound of the formula

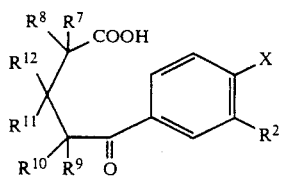

and replacing the oxo group in the compound of formula VI by a substituent $R^5$ and/or $R^6$.

A compound of the formula

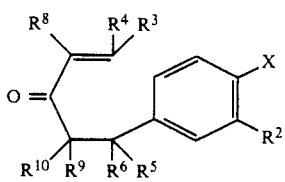

can be cyclized to a compound of formula VIII by treatment with a Friedel-Crafts catalyst such as aluminum chloride. A compound of formula VII can be obtained by Friedel-Crafts reaction of a compound of the formula

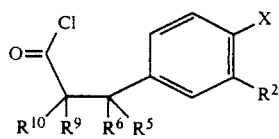

with compounds of the formula $R^8$—CH=C($R^3$,$R^4$).

The previously described method s and further methods for preparing the compounds of formula II are described in detail in the Examples.

The compounds of formula I and their salts are therapeutically active. In particular. The compounds of formula I and their salts have anti-seborrheic, anti-keratinizing, anti-neoplastic and anti-allergic/ anti-inflammatory activity, and are therefore useful as anti-seborrheic, anti-keratinizing, anti-neoplastic and anti-allergic/anti-inflammatory agents. The invention is accordingly also relates to the compounds of formula I and their salts for use in the preparation of pharmaceuticals having such a spectrum of activity.

For example, the activities set forth in Table I were determined in the test procedure described in Europ. J. Cancer 10, 731-7 (1974) for the treatment of chemically-induced skin papillomas in mice.

TABLE I

| Compound of Example | Dosage per 14 days [mg/kg] 4 × | Regression of the papilloma diameter [%] | A-hypervitaminosis Dosage per 14 days [mg/kg] 10 × |
| --- | --- | --- | --- |
| 2 | 3 | 59 | 3 |
|   | 1.5 | 57 |   |
|   | 0.75 | 25 |   |
| 4 | 0.75 | 67 | 0.75 |
|   | 0.4 | 56 |   |
|   | 0.2 | 28 |   |
| 5 | 0.2 | 66 | 0.1 |
|   | 0.1 | 47 |   |
| 6 | 0.1 | 54 | 0.1 |
| 10 | 50 | 78 | 50 |
|   | 25 | 70 |   |
|   | 12.5 | 43 |   |

The compounds of formula I and their salts can be used for topical and systemic therapy of benign and malignant neoplasms, of premalignant lesions as well as, for the systemic and topical prophylaxis of the said conditions.

Furthermore, the compounds of formula I and their salts are suitable for the topical and systemic therapy of acne, psoriasis and other dermatoses which are accompanied by an intensified or pathologically altered cornification, as well as of inflammatory and allergic dermatological conditions. Further, the compounds formula I and their salts can also be used for the control of mucous membrane disorders with inflammatory or degenerative or metaplastic changes.

The pharmaceutical compositions containing compounds of formula I or their salts can be administered enterally. parenterally or topically. For enteral administration there are suitable for example, in the form of tablets, capsules, dragees, syrups, suspensions, solutions and suppositories. Preparations in the form of infusion or injection solutions are suitable for parenteral administration.

The dosages at which the preparations, that is, the pharmaceutical compositions, are administered can vary according to the mode of use and route of use as well as according to the requirements of the patients. In general, daily dosages of about 0.1-50 mg/kg, preferably 1-15 mg/kg, come into consideration for adults.

The preparations can be administered in one dosage or several dosages. Capsules containing about 5-200 mg of active substance are a preferred administration form.

The preparations can contain inert or pharmacodynamically active additives. Tablets or granulates, for example, can contain a series of binding agents, filler materials, carrier substances or diluents. Liquid preparations can be present for example, in the form of a sterile solution which is miscible with water. Capsules can contain a filler material or thickening agent in addition to the active substance. Furthermore, there can also be present flavor-improving additives as well as substances usually used as preserving, stabilizing, moisture-retaining and emulsifying agents salts for varying the osmotic pressure, buffers and other additives.

The previously mentioned carrier substances and diluents can consist of organic or inorganic substances, for example, water gelatin lactose, starch magnesium stearate, talc gum arabic, polyalkylene glycols and the like. It is a prerequisite that all adjuvants used in the manufacture of the preparations be non-toxic.

For topical use, the active substances of formula 1 are conveniently used in the form of salves, tinctures, creams, solutions, lotions, sprays, suspensions and the like. Salves and creams as well as solutions are preferred. These preparations intended for topical use can be prepared by mixing substances of formula I or a salt thereof as the active ingredient with non-toxic, inert, solid or liquid carriers which are usual in such preparations and which are suitable for topical treatment.

For topical use, suitable preparations conveniently are, about 0.1–5%, preferably 0.3–2%, solutions, as well as about 0.1–5%, preferably about 0 3–2%, salves or creams.

If desired, an antioxidant, for example tocopherol, N-methyl-γ-tocopheramine as well as butylated hydroxyanisole or butylated hydroxytoluene be admixed with the preparations.

The following Examples further illustrate the invention. The temperatures are given in degrees Celsius, unless otherwise stated.

EXAMPLE 1

A. Preparation of the starting material:

(a) 19.0 ml of thionyl chloride are added to 30 g of p-bromohydrocinnamic acid and heated to reflux for 30 minutes. After cooling, the excess reagent is removed by evaporation (finally at 0.5 Torr) and the crude acid chloride is dissolved in 300 ml of carbon disulfide. After cooling to −10°, 3.5 ml of tin tetrachloride are added under an argon atmosphere. Thereafter, 25 ml of isobutylene are introduced and the reaction mixture is warmed slowly to room temperature. After renewed cooling to 0°, 35 g of aluminum trichloride are added. The reaction mixture is stirred overnight, poured on to ice, extracted with diethyl ether and the extract is washed with water and phosphate buffer (pH 7) and dried. After evaporation, the residue is chromatographed on silica gel with petroleum ether (low-boiling) and ethyl acetate (9:1). There is obtained 2-bromo-5,6,8,9-tetrahydro-9,9-dimethyl-7-benzocycloheptenone in the form of yellowish crystals of m.p. 67°–68° (from hexane).

(b) 12.4 g of the compound obtained are dissolved in 60 ml of diethylene glycol and treated with 6.9 ml of hydrazine hydrate and 8.9 g of potassium hydroxide. The reaction mixture is heated to 195° and the disappearance of the hydrazone is followed by gas chromatography. After about 12 hours, the reaction mixture is cooled, treated with water and extracted with low-boiling petroleum ether. The extract is washed with water, dried and evaporated. After chromatography on silica gel with petroleum ether (low-boiling). there is obtained 2-bromo-6,7,8,9-tetrahydro-9,9-dimethyl-5H-benzocycloheptene as a colorless oil.

(c) This oil is converted into the Grignard reagent with 675 mg of Mg shavings under argon in 30 ml of absolute tetrahydrofuran. After cooling to −10°, acetaldehyde is added in a large excess. The reaction mixture is thereafter hydrolyzed with saturated ammonium chloride solution. extracted with diethyl ether and the extract is washed with water and dried. After chromatography on silica gel with petroleum ether (low-boiling) and ethyl acetate (9:1). there is obtained 6,7,8,9-tetrahydro-α9,9-trimethyl-5H-benzocycloheptene-2-methanol as a colorless oil.

B. Wittig reaction:

783 mg of 6,7,8,9-tetrahydro-α9,9-trimethyl-5H-benzocycloheptene-2-methanol are dissolved in 8 ml of acetonitrile, treated with 1.77 g of triphenylphosphine hydrobromide and stirred at 40° for 24 hours. Thereafter, the solvent is evaporated under reduced pressure and the residue is partitioned between hexane and ethanol/water (8:2). The heavier phase is evaporated and evaporated twice with methylene chloride. After drying under reduced pressure, there are obtained 1.91 g of phosphonium salt which is further processed as the crude product.

The phosphonium salt is heated to reflux for 20 hours with 910 mg of ethyl 4-formylbenzoate in 5 ml of butylene oxide. After cooling, the reaction mixture is partitioned between ethanol/water (8:2) and hexane, the lighter phase is dried and evaporated. After chromatography on silica gel with petroleum ether (low-boiling) and ethyl acetate (97:3), there are obtained 820 mg of ethyl p-[(E)-2-(6,7,8,9-tetrahydro-9,9-dimethyl-5H-benzocycloheptene-2-yl)propenyl]benzoate of m.p. 69°–70° (from hexane).

EXAMPLE 2

In analogy to Example 1B, from 6,7,8,9-tetrahydro-α,5,5-trimethyl-5H-benzocycloheptene-2-methanol (prepared in analogy to Example 1A from 2-bromo-5,6,8,9-tetrahydro-5,5-dimethyl-7-benzocycloheptenone), there is obtained ethyl P-[(E)-2-(6,7,8,9-tetrahydro-5,5-dimethyl-5H-benzocyclohepten-2-yl)propenyl]benzoate of m.p. 48°–50°.

EXAMPLE 3

In analogy to Example 1B, from 6,7,8,9-tetrahydro-α,5,9,9-tetramethyl-5H-benzocycloheptene-2-methanol (prepared from 2-bromo-5,6,8,9-tetrahydro-5,9,9-trimethyl-7-benzocycloheptenone in analogy to Example 1A), there is obtained ethyl p-[(E)-2-(6,7,8,9-tetrahydro-5,9,9-tri-methyl-5H -benzocycloheptene-2-yl)propenyl]benzoate of m.p. 77°–78°.

EXAMPLE 4

In analogy to Example 1B, from 6,7,8,9-tetrahydro-α5,5,9-tetramethyl-5H-benzocycloheptene-2-methanol (prepared from 2-bromo-5,6,8,9-tetrahydro-5,5,9-trimethyl-7-benzocycloheptenone in analogy to Example 1A), there is obtained ethyl p-[(E)-2-(6,7,8,9-tetrahydro-5,5,9-tri-methyl-5H-benzocyclohepten-2-yl)propenyl]benzoate of m.p. 43°–46°.

EXAMPLE 5

In analogy to Example 1B, from 6,7,8,9-tetrahydro-α5,5,9,9-pentamethyl-5H-benzocycloheptene-2-methanol, there is obtained ethyl P-[(E)-2-(6,7,8,9-tetrahydro-5,5,9,9-tetramethyl-5H -benzocycloheptene-2yl)propenyl]-benzoate of m.p. 103°–104°.

The starting material can be prepared as follows:

47.1 g of bromobenzene and 37.8 g of phorone are stirred at room temperature for 48 hours in the presence of 40 g of aluminum trichloride in 600 ml of carbon disulfide. The reaction mixture is then poured on to ice, extracted with diethyl ether. The extract is washed with water, dried and evaporated. After chromatography on silica gel with petroleum ether (low-boiling) and ethyl acetate (9:1) and recrystallization from hexane, there is obtained 2-bromo-5,6,8,9-tetrahydro-5,5,9,9-tetramethyl-7H-benzocyclohepten-7-one of m.p. 104°–105°.

The last-named compound can be reacted further in analogy to Example 1A, paragraph b) to give 6,7,8,9-tetra-hydro-α5,5,9,9-pentamethyl-5H-benzocycloheptene-2-methanol.

EXAMPLE 6

In analogy to Example 1B, from 6,7,8,9-tetrahydro-α7,7,9-tetramethyl-5H-benzocycloheptene-2-methanol, there is obtained p-[(E)-2-(6,7,8,9-tetrahydro-7,7,9-trimethyl-5H-benzocyclohepten-2-yl)propenyl]benzoate of m.p. 68°–71°.

The starting material can be prepared as follows:

15 ml of about 1.5M freshly prepared methylmagnesium iodide solution in diethyl ether are slowly added dropwise at room temperature to a solution of 4.28 g of 3-bromo-6,7,8,9-tetrahydro-7,7-dimethyl-5H-benzocycloheptene-5-one in 20 ml of absolute diethyl ether. The reaction mixture is stirred for 30 minutes. Thereafter, it is hydrolyzed with saturated ammonium chloride solution, extracted with diethyl ether and the extract is washed with water and dried and evaporated. There are obtained 4.8 g of a colorless oil which are treated with 80 ml of 37% hydrochloric acid and stirred intensely overnight. Thereafter, the mixture is extracted with diethyl ether. The extract is washed with water, dried and evaporated. After filtration over silica gel with low-boiling petroleum ether, there are obtained 3.82 g of a colorless oil which consists of a 2:1 mixture of exo- and endocyclic olefins in accordance with analysis by gas chromatography. 3.30 g of this oil are reacted under argon in 10 ml of absolute tetrahydrofuran with 330 mg of magnesium shavings and the Grignard reagent is reacted at −10° with a large excess of acetaldehyde. After 15 minutes, the reaction mixture is hydrolyzed wi(h saturated ammonium chloride solution, and extracted with diethyl ether. The extract is washed with water, dried and evaporated. After chromatography on silica gel with petroleum ether (low-boiling) and ethyl acetate (8:2), there are obtained 2.15 g of sec. alcohol as a colorless oil (mixture of endo- and exocyclic olefins). This oil is hydrogenated in 20 ml of absolute ethanol over 150 mg of palladium-charcoal at normal pressure. After the uptake of one equivalent of hydrogen the catalyst is removed by filtration. The reaction mixture is evaporated and chromatographed on silica gel with petroleum ether (low-boiling) and ethyl acetate (8:2). There are obtained 1.17 g of 6,7,8,9-tetrahydro-α,7,7,9-tetramethyl-5H-benzocycloheptene-2-methanol as a 1:1 mixture of diastereomers in the form of a colorless oil.

EXAMPLE 7

In analogy to Example 1B, from 6,7,8,9-tetrahydro-α,7,7,9,9-pentamethyl-5H -benzocycloheptene-2-methanol, there is obtained methyl P-[(E)-2-(6,7,8,9-tetrahydro-7,7,9,9-tetramethyl-5H-benzocycloheptene-2-yl)propenyl]-benzoate of m.p. 88–89°.

The starting material can be prepared as follows:

A solution of 26.5 g of dry methoxymethyltriphenylphosphonium chloride in 85 ml of absolute tetrahydrofuran is treated slowly at 0° with 1.1 equivalent of 1.55 M n-butyllithium in hexane. After 30 minutes, 13.77 g of 3-bromo-6,7,8,9-tetrahydro-7,7-dimethyl-5H -benzocycloheptene-5-one are added and the reaction mixture is stirred for 1 hour without cooling. The reaction mixture is then poured on to ice and extracted with diethyl ether. The extract is washed with water, dried and evaporated. After chromatography on silica gel with petroleum ether (low-boiling) containing up to 5% of ethyl acetate, there are obtained 12.2 g of enol ether as a colorless oil. (E/Z mixture).

The enol ether is dissolved in 820 ml of acetic acid. The solution is treated with 80 ml of 10% sulfuric acid and heated to reflux overnight. Thereafter, the majority of the solvent is distilled off. The residue is partitioned between water and diethyl ether. The ethereal solution is washed with 10% sodium carbonate solution, dried and evaporated. There are obtained 11.4 g of aldehyde in the form of a colorless oil.

This oil is dissolved in 70 ml of absolute t-butanol and treated under an argon atmosphere at 0° with 9.1 g of potassium t-butylate. The reaction mixture is stirred without cooling for half an hour and then treated with 7.6 ml of methyl iodide. After stirring at room temperature for 2 hours, the mixture is poured on to ice and extracted with diethyl ether. The ethereal extract is washed with water, dried and evaporated. Chromatography on silica gel with hexane/ethyl acetate (99.5:0.5) yields 2.30 g of 3-bromo-6,7,8,9-tetrahydro-5,7,7-trimethyl-5H-benzocycloheptene-5-carboxaldehyde as a colorless oil.

2.30 g of the aldehyde obtained are dissolved in 12 ml of diethylene glycol and treated with 0.80 ml of hydrazine hydrate. The reaction mixture is heated to 100° for 3 hours. Then, it is treated with 1.1 g of potassium hydroxide and heated to reflux (bath temperature 180°) for 14 hours. After cooling, the reaction mixture is poured on to ice and extracted with petroleum ether (low-boiling). The extract is washed with water, dried and evaporated. After filtration over silica gel with petroleum ether (low-boiling), there are obtained 1.25 g of a colorless oil which is converted into the Grignard reagent under an argon atmosphere in 12 ml of absolute tetrahydrofuran with 140 mg of magnesium shaVings. After 1.5 hours, acetaldehyde is added at −10° in a large excess to the Grignard reagent and the reaction mixture is stirred at room temperature for 15 minutes. Thereafter, the reaction mixture is hydrolyzed with saturated ammonium chloride solution, extracted with diethyl ether. The extract is washed with water, dried and evaporated. After chromatography on silica gel with petroleum ether (low-boiling) and ethyl acetate (8:2). there are obtained 760 mg of 6,7,8,9-tetrahydro-α,7,7,9,9-pentamethyl-5H-benzocycloheptene-2-methanol as a colorless oil.

EXAMPLE 8

Preparation of the starting material:

(a) 82 g of 3,3-dimethyl-5-phenylvaleric acid are treated with 57 ml of thionyl chloride and heated to reflux for half an hour. Thereafter, the excess reagent is evaporated, finally under a high vacuum for 1.5 hours. The acid chloride prepared, dissolved in 300 ml of methylene chloride, is added within 3.5 hours under an argon atmosphere to 79 g of aluminum trichloride in 650 ml of methylene chloride. Thereafter, the reaction mixture is stirred for an additional 10 minutes and poured on to ice. The organic phase is washed with water dried and evaporated. After chromatography on silica gel with petroleum ether (low-boiling)/ethyl acetate (98:2), there are obtained 62 g of 6,7,8,9-tetrahydro-7,7-dimethyl-5H-benzocycloheptene-5-one.

(b) 34 g of the previously obtained compound are heated to reflux (bath temperature 180°–190°) for 3 days with 19.5 ml of hydrazine hydrate and 22.4 g of potassium hydroxide in 200 ml of diethylene glycol. Thereafter, the reaction mixture is cooled, partitioned between diethyl ether and water. The organic phase is washed with water, dried and evaporated. Chromatography on silica gel with petroleum ether (low-boiling) yields 22.2 g of 6,7,8,9-tetrahydro-7,7-dimethyl-5H-benzocycloheptene as a colorless oil which crystallizes upon standing.

(c) 6.20 g of the previously obtained compound are treated under an argon atmosphere in 65 ml of 1,2-dichloroethane at −10° with 2.9 ml of acetyl chloride and, thereafter, with 6.0 g of aluminum trichloride. The reaction mixture is allowed to warm up, poured on to ice after 30 minutes, and extracted with diethyl ether. The extract is washed with water, dried and evaporated. There are obtained 8.40 g of 2-acetyl-6,7,8,9-tetrahydro-7,7-dimethyl-5H-benzocycloheptene as a colorless oil.

B. Horner reaction:

770 mg of sodium hydride (50% in mineral oil) are treated at room temperature under an argon atmosphere with 5.30 g of ethyl o-(diethoxyphosphinyl)-p-toluate. After stirring for 2 hours 2.55 g of 2-acetyl-6,7,8,9-tetrahydro-7 7-dimethyl-5H benzocycloheptene, dissolved in small amount of dimethylformamide, are added dropwise. After 2 hours, the reaction mixture is poured on to ice and extracted with diethyl ether. The ethereal extract is washed with water, dried and evaporated. After chromatography on silica gel with petroleum ether (low-boiling)/ ethyl acetate (9:1), there are obtained 3.40 g of ethyl p-[(E)-2-(6,7,8,9-tetrahydro-7,7-dimethyl-5H-benzocyclo-hepten-2-yl)propenyl]benzoate of m.p. 87-°88° (from hexane).

EXAMPLE 9

In analogy to Example 8B, from 2-acetyl-5,6,8,9-tetrahydrospiro[7H-benzocyclohepten-7,1'-cyclopentane](prepared in analogy to Example 8A starting from p-phenethyl-cyclopentaneacetic acid), there is obtained ethyl p-[(E)-2-[5,6,8,9-tetrahydrospiro[7H-benzocyclohepten-7,1'-cyclopentane]-2-yl]propenyl]benzoate of m.p. 88°–89°.

EXAMPLE 10

In analogy to Example 8B, from 2-acetyl-6,7,8,9-tetrahydro-7-methyl-7-ethyl-5H -benzocycloheptene (prepared in analogy to Example 8A starting from 3-methyl-3-ethyl-5-phenylvaleric acid), there is obtained ethyl p-[(E)-2-(7-ethyl-6,7,8,9-tetrahydro-7-methyl-5H-benzocyclohepten-2-yl)propenyl]benzoate of m.p. 82°–83°.

EXAMPLE 11

In analogy to Example 8B, from 2-acetyl-6,7,8,9-tetrahydro-7-methyl-5H-benzocycloheptene (prepared in analogy to Example 8A starting from 3-methyl-5-phenylvaleric acid) there is obtained ethyl p-[(E)-2-(6,7,8,9-tetrahydro-7-methyl-5H-benzocyclohepten-2-yl)propenyl] benzoate of m.p. 40°–41°.

EXAMPLE 12

In analogy to Example 8B, from 2-acetyl-6,7,8,9-tetrahydro-7,7-ethylenedioxy-5H-benzocycloheptene and subsequent acetal cleavage, there is obtained ethyl p-[(E)-2-(6,7,8,9-tetrahydro-7-oxo-5H-benzocyclohepten-2-yl)-propenyl]benzoate of m.p. 90°–91°.

EXAMPLE 13

In analogy to Example 8B, from 2-acetyl-5,6,8,9-tetrahydro-6,6,8,8-tetramethyl-7H-benzocyclohepten-7-one, there is obtained ethyl p-[(E)-2-(6,7,8,9-tetrahydro-6,6,8,8-tetramethyl-7-oxo-5H-benzocyclohepten-2-yl)propenyl]-benzoate of m.p. 79°–80°.

The starting material can be prepared as follows 2.20 g of 5,6,8,9-tetrahydro-7H-benzocyclohepten-7-one are added to 80 mmol of potassium hydride (20% in mineral oil) in 80 ml of absolute tetrahydrofuran under an argon atmosphere. After 15 minutes, the mixture is cooled to −10° and 4.67 ml of methyl iodide are added dropwise. The reaction mixture is warmed to 10° in 1 5 hours and then hydrolyzed cautiously while cooling with ice and under an argon atmosphere. The reaction mixture is treated with diethyl ether. The organic phase is separated, washed with water, dried and evaporated. The crude product is purified by chromatography on silica gel. Elution is carried out firstly with petroleum ether (low-boiling) and thereafter with petroleum ether/ethyl acetate (97.5:2.5), whereby there are obtained 2.57 g of 5,6,8,9-tetrahydro-6,6,8,8-tetramethyl-7H-benzocyclohepten-7-one as a colorless oil which crystallizes upon standing.

620 mg of the previously prepared compound are treated in 10 ml of carbon disulfide under an argon atmosphere at 0° with 0.61 ml of acetyl chloride and 1.02 g of aluminum trichloride. Thereafter, the reaction mixture is stirred at room temperature for 3 hours poured on to ice and extracted with diethyl ether. The ethereal solution is washed with 10% sodium carbonate solution and water, dried and evaporated. After chromatography on silica gel with petroleum ether (low-boiling)/ethyl acetate (8:2), there are obtained 680 mg of 2-acetyl-5,6,8,9-tetrahydro-6,6,8,8-tetramethyl-7H-benzocycloheptene-7-one.

EXAMPLE 14

In analogy to Example 8B, from 2-acetyl-5,6,8,9-tetrahydrospiro[7H-benzocyclohepten-7,1'-cyclopropane], there is obtained ethyl p-[(E)-2-[5,6,8,9-tetrahydrospiro[7H-benzocycloheptene-,1'-cyclopropane]-2-yl]propenyl]benzoate of m.p. 56°–58°.

EXAMPLE 15

In analogy to Example 8B, from 2-acetyl-6,7,8,9-tetrahydro-5H-benzocycloheptene, there is obtained ethyl p-[(E)-2-(6,7,8,9-tetrahydro-5H-benzocyclohepten-2-yl)propenyl]benzoate of m.p. 53°–54°.

EXAMPLE 16

300 mg of ethyl p-[(E)-2-(6,7,8,9-tetrahydro-5H-benzocyclohepten -2-yl)propenyl]benzoate are treated in 20 ml of ethanol with 2 ml of 2.5M sodium hydroxide solution. The mixture is stirred at room temperature for 48 hours, diluted with water and extracted with diethyl ether. The aqueous phase is acidified, extracted with ether. The ethereal phase is washed with water, dried and evaporated. There are obtained 200 mg of p-[(E)-2-(6,7,8,9-tetrahydro-5H-benzocyclohepten-2-yl)propenyl]benzoic acid of m.p. 198°.

The following compounds can be obtained in an analogous manner:

p-[(E)-2-(6,7,9-Tetrahydro-7,7-dimethyl-5H-benzocyclohepten-2-yl )propenyl]benzoic acid, m.p. 192°–193°, p-[(E)-2-(6,7,8,9-tetrahydro-5,5,9,9-tetramethyl-5H-benzocycloheptene-2-yl)propenyl]benzoic acid, m.p. 221°–222°.

EXAMPLE 17

In analogy to Example 8Ac, from 5,7,8,9-tetrahydro-6,6,8,8-tetramethyl-5H-benzocycloheptene, there is obtained 2-acetyl-6,7,8,9-tetrahydro-6,6,8,8-tetramethyl-5H -benzocycloheptene, and therefrom, in analogy to Example 8B, there is obtained ethyl p-[(E)-2-(6,7,8,9-tetrahydro-6,6,8,8-tetramethyl-5H-benzocycloheptene-yl) propenyl]-benzoate, and therefrom, in analogy to Example 16, there is obtained p-[(E)-2-(6,7,8,9-tetrahydro-6,6,8,8-tetramethyl-5H-benzocycloheptene-2-yl) propenyl]benzoic acid, m.p. 232°–235°C.

The starting material can be prepared as follows:

2.57 g of 5,6,8,9-tetrahydro-6,6,8,8-tetramethyl-7H-benzocycloheptene-7-one are dissolved in 50 ml of absolute diethyl ether and treated cautiously at 0° with 460 mg of lithium aluminum hydride. The cooling bath is removed and the mixture is stirred at room temperature for an additional 2 hours. Then, 1.2 g of sodium hydroxide, dissolved in a small amount of water, are added portionwise, whereupon the reaction mixture is stirred until a filterable precipitate has formed. After filtration and evaporation of the filtrate, there is obtained 6,7,8,9-tetrahydro-6,6,8,8-tetramethyl-5H -benzocycloheptene-7-ol as a crude product which melts at 66°–68° after recrystallization from petroleum ether (low-boiling).

1.52 g of the foregoing alcohol are dissolved under an argon atmosphere in 7 ml of dimethyl sulfoxide and the solution is treated with 404 mg of sodium hydride (50% in mineral oil). The reaction mixture is heated to 50° for 2 hours. Thereafter, it is cooled to 0° and treated with 1.18 ml of carbon disulfide. The reaction mixture is left at room temperature for 45 minutes. Thereafter, it is cooled to 0° and treated dropwise with 865 μl of methyl iodide. After stirring at room temperature for 45 minutes the reaction mixture is poured on to ice and extracted with diethyl ether. The extract is washed with water and dried and evaporated. Chromatography on silica gel with petroleum ether (low-boiling) and ethyl acetate (99:1) yields S-methyl-0-(6,7,8,9-tetrahydro-6,6,8,8-tetramethyl-5H-benzocyclohepten-7-yl)dithiocarbonate as a yellowish solid.

1.76 g of the previously mentioned dithiocarbonate are dissolved under an argon atmosphere in 145 ml of toluene. The mixture is heated to the boiling point and there are added dropwise thereto within one hour 50 ml of toluene in which 2.67 ml of tributyltin hydride and 100 mg of azaisobutyronitrile have been dissolved. After 30 minutes the reaction mixture is cooled. The majority of the toluene is evaporated and the thus-obtained crude product is chromatographed on silica gel. Elution with petroleum ether (low-boiling) yields 6,7,8,9-tetrahydro-6,6,8,8-tetramethyl-5H-benzocycloheptene.

EXAMPLE 18

In analogy to Example 8B from 2-acetyl-6,7,8,9-tetrahydro-5,9-dimethyl-5,9-methano-5H-benzocyclohepten-10-yl acetate, there is obtained ethyl p-[(E)-2-(6,7,8,9-tetrahydro-10-acetoxy-5,0-dimethyl-5,9-methano-5-benzocyclohepten-2-yl)propenyl]benzoate and, therefrom, in analogy to Example 16, there is obtained p-[(E)-2-(6,7,8,9-tetrahydro-10-hydroxy-5,9-dimethyl-5,9-methano-5-benzocyclohepten-2-yl)propenyl]benzoate, m.p. 188°–190°.

The starting material can be prepared as follows:

895 mg of 6,7,8,9-tetrahydro-5,9-dimethyl-5,9-methano-5H-benzocycloheptene-0-ol (Chem. Comm. 1972, 1238) are treated under an argon atmosphere in 12 ml of dichloroethane at 0° with 0.40 ml of acetyl chloride and 1.30 g of aluminum trichloride. The reaction mixture is stirred for half an hour, poured on to ice and extracted with diethyl ether, washed with water and dried. Evaporation of the solvent and chromatography on silica gel (low-boiling petroleum ether/ethyl acetate 9:1) yields 2-acetyl-6,7,8,9-tetrahydro-5,9-dimethyl-5,9-methano-5H-benzocyclohepten-10-yl acetate as a colorless solid.

EXAMPLE 19

In analogy to Example 8B, from 2-acetyl-6,7,8,9-tetrahydro-5,9-dimethyl-5,9-methano-5H-benzocycloheptene, there is obtained ethyl p-[(E)-2-(6,7,8,9-tetrahydro-5,9-dimethyl-5,9-methano-5H-benzocyclohepten-2-yl)propenyl]benzoate and, therefrom, in analogy to Example 16, there is obtained p-[(E)-2-(6,7,8,9-tetrahydro-5 9-dimethyl-5,9-methano-5H-benzocyclohepten-2-yl)propenyl]benzoic acid of m.p. 195°–200°.

The starting material can be prepared as follows:

6,7,8,9-Tetrahydro-5,9-dimethyl-5,9-methano-5H-benzocyclohepten-10-ol is converted with sodium hydride and dimethyl sulfoxide into the anion and this is reacted with carbon disulfide to give a dithiocarbonate which is methylated with methyl iodide. Treatment of the thus-obtained compound with tributyl tin hydride in the presence of azaisobutyronitrile in toluene yields 6,7,8,9-tetrahydro-5,9-dimethyl-5,9-methano-5H-benzocycloheptene which is reacted with acetyl chloride according to Friedel-Crafts as described in Example 8Ac.

EXAMPLE 20

In analogy to Example 1B (1st paragraph), from 6,7,8,9-tetrahydro-α,3,7,7-tetramethyl-5H-benzocycloheptene-2-methanol, there is obtained the corresponding phosphonium salt. 5.30 g of the phosphonium salt are suspended in 35 ml of tetrahydrofuran and deprotonized at 0° with 9.0 ml of 1.4M nBuLi (hexane) After 30 minutes, 2 30 g of methyl 4-formylbenzoate are added thereto and the mixture is stirred at room temperature for an additional 2 hours. The mixture is poured on to ice-water, extracted with Et₂O, washed with water, dried and evaporated. Chromatography on silica gel (low-boiling petroleum ether/AcOEt=93/3), followed by crystallization from n-hexane, yields 560 mg of methyl p-[(E)-(6,7,8,9-tetrahydro-3,7,7-trimethyl-5H-benzocyclohepten-2-yl) propenyl]benzoate of m.p. 59°–60°.

The starting material can be prepared from o-bromotoluene and 3,9-dimethylglutaric anhydride.

EXAMPLE 21

In analogy to Example 1B, from 6,7,8,9-tetrahydro-α,9-dimethyl-5H-benzocycloheptene-2-methanol, there is obtained ethyl p-[(E)-2-(6,7,8,9-tetrahydro-9-methyl-5H-benzocyclohepten-2-yl)propenyl]benzoate of m.p. 48°–50°.

The starting material can be prepared from benzosuberone by the reaction sequence (a) bromination; (b) addition of MeMg; (c) deoxygenation; (d) metallation with Mg and addition of acetaldehyde.

EXAMPLE 22 p-[(E)-2-(6,7,8,9-Tetrahydro-7,7,9,9-tetramethyl-5H-benzocycloheptene-2-yl)propenyl]benzoic acid of m.p. 182°–183° is obtained from the corresponding methyl ester (Example 7) in analogy to Example 16.

EXAMPLE 23

In analogy to Example 8B and Example 16, from -acetyl-6,7,8,9-tetrahydro-7,7-dimethyl-3-octyl-5H-benzocycloheptene, there is obtained p-[(Z)-(6,7,8,9tetrahydro-7,7-dimethyl-3-octyl-5H-benzocyclohepten-2-yl) propenyl]-benzoic acid of m.p. 113°–114°.

The starting material can be prepared from octylbenzene and 3,3-dimethylglutaric anhydride.

EXAMPLE 24

In analogy to Example 8B and Example 16, from 2-acetyl-3-bromo-6,7,8,9-tetrahydro-7,7-dimethyl-5H-benzocycloheptene, there is obtained p-[(Z)-2-(3-bromo-6,7,8,9-tetrahydro-7,7-dimethyl-5H-benzocyclohepten-2-yl)propenyl]benzoic acid of m.p. >270°.

The starting material can be prepared from bromobenzene via the following reaction sequence. (1) Acylation with 3,3-dimethylglutaric anhydride; (2) Wolf-Kishner reduction; (3) intramolecular Friedel-Crafts acylation; (4) Wolf-Kishner reduction; (5) Friedel-Crafts acetylation.

EXAMPLE 25

In analogy to Example 16, by hydrolyzing the Z-enriched ester (mother liquor of Example 20), there is obtained p-[(Z)-2-(6,7,8,9-tetrahydro-3,7,7-trimethyl-5H-benzocycloheptene-2-yl)propenyl]benzoic acid of m.p. 223°–225°.

EXAMPLE A

Hard gelatin capsules can be prepared as follows:

| Ingredients | mg/capsule |
| --- | --- |
| 1. Spray-dried powder containing 75% of a compound of formula I | 200 |
| 2. Sodium dioctylsulfosuccinate | 0.2 |
| 3. Sodium carboxymethylcellulose | 4.8 |
| 4. Microcrystalline cellulose | 86.0 |
| 5. Talc | 8.0 |
| 6. Magnesium stearate | 1.0 |
| Total | 300 |

The spray-dried powder, which is based on the active substance gelatin and microcrystalline cellulose, and which has an average particle size of the active substance of <1μ (measured by means of autocorrelation spectroscopy), is moistened with an aqueous solution of sodium carboxymethylcellulose and sodium dioctylsulfosuccinate and kneaded. The resulting mass is granulated, dried and sieved. The granulate obtained is mixed with microcrystalline cellulose, talc and magnesium stearate. The powder is filled into size O capsules.

EXAMPLE B

Tablets can be prepared as follows:

| Ingredients | mg/tablet |
| --- | --- |
| 1. A compound of formula I as a finely milled powder | 500 |
| 2. Lactose powd. | 100 |
| 3. Maize starch white | 60 |
| 4. Povidone K30 | 8 |
| 5. Maize starch white | 112 |
| 6. Talc | 16 |
| 7. Magnesium stearate | 4 |
| Total | 800 |

The finely milled substance is mixed with lactose and a portion of the maize starch. The mixture is moistened with an aqueous solution of Povidone K30 and kneaded, and the resulting mass is granulated, dried and sieved. The granulate is mixed with the remaining maize starch talc and magnesium stearate and pressed to tablets of suitable size.

EXAMPLE C

Soft gelatin capsules can be prepared as follows:

| Ingredients | mg/capsule |
| --- | --- |
| 1. A compound of formula I | 50 |
| 2. Triglyceride | 450 |
| Total | 500 |

10 g of compound I are dissolved in 90 g of medium-chain triglyceride with stirring, inert gasification and protection from light. This solution is processed as the capsule fill mass to soft gelatin capsules containing 50 mg of active substance.

EXAMPLE D

A lotion can be prepared as follows:

| Ingredients | |
| --- | --- |
| 1. A compound of formula I, finely milled | 3.0 g |
| 2. Carbopol 934 | 0.6 g |
| 3. Sodium hydroxide | q.s. ad pH 6 |
| 4. Ethanol, 94% | 50.0 g |
| 5. Demineralized water | ad 100.0 g |

The active substance is incorporated into the ethanol 94%/water mixture under protection from light. Carbopol 934 is stirred in until gelling is complete and the pH value is adjusted with sodium hydroxide.

We claim:

1. A compound of the formula

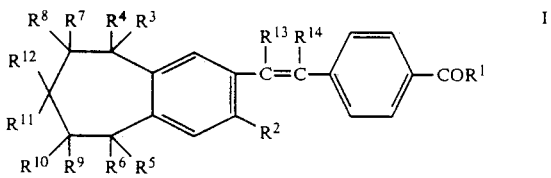

wherein
R[1] is hydroxy, lower-alkoxy, amino, mono- or di-lower-alkylamino;
R[2] is hydrogen, alkyl, alkoxy or halogen; R[3], R[4], R[5], R[6], and R[12] independently are hydrogen or lower-alkyl;
R[3] and R[5] taken together are methylene or hydroxymethylene;
R[7], R[9] and R[10] independently are hydrogen or lower-alkyl;
R[11] and R[12] taken together are oxo or spiro-cyclo-lower alkyl; or R[11] is hydrogen and R[12] is hydroxy or acetoxy; and one of the residues R[13] and R[14] is hydrogen and the other is lower-alkyl or trifluoromethyl,
or, when R[1] is hydroxy, a physiologically compatible salt thereof.

2. A compound in accordance with claim 1, wherein R[1] is hydroxy, lower-alkoxy, amino, mono- or di-lower-alkyl-amino; R[2] is hydrogen, alkyl, alkoxy or halogen; R[3], R[4], R[5], R[6], R[11] and R[12] independently are hydrogen or lower-alkyl; R[3] and R[5] taken together are methylene; R[7], R[8], R[9] and R[10] independently are hydrogen or lower-alkyl; $R^{11}$ and $R^{12}$ taken together are oxo or $R^{11}$ is hydrogen and $R^{12}$ is hydroxy; and one of the residues $R^{13}$ and $R^{14}$ is hydrogen and the other is lower-alkyl or trifluoromethyl.

3. A compound in accordance with claim 2, wherein $R^1$ is hydroxy or lower-alkoxy.

4. A compound in accordance with claim 3, wherein $R^2$ is hydrogen.

5. A compound in accordance with claim 4, wherein $R^3$, $R^4$, $R^5$, $R^6$, $R^7$, $R^8$, $R^9$, $R^{10}$, $R^{11}$ and $R^{12}$ independently are hydrogen or lower-alkyl.

6. A compound in accordance with claim 5, wherein at least one of the residues is lower-alkyl.

7. A compound in accordance with claim 4, wherein $R^{11}$ and $R^{12}$ taken together are oxo.

8. A compound in accordance with claim 4, wherein $R^{11}$ is hydrogen and $R^{12}$ is hydroxy.

9. A compound in accordance with claim 4, wherein $R^3$ and $R^5$ taken together are methylene.

10. A compound in accordance with claim 1 ethyl p-[(E)-2-(6,7,8,9-tetrahydro-7,7-dimethyl-5H-benzocyclohepten-2-yl)propenyl]benzoate.

11. A compound in accordance with claim 1, selected from the group consisting of ethyl p-[(E)-2-(6,7,8,9-tetrahydro-9,9-dimethyl-5H-benzocyclohepten-2-yl)propenyl]benzoate;
ethyl p-[(E)-2-(6,7,8,9-tetrahydro-5,5-dimethyl-5H-benzocycloheptene-2-yl)propenyl]benzoate;
ethyl p-[(E)-2-(6,7,8,9-tetrahydro-5,9,9-trimethyl-5H-benzocycloheptene-2-yl)propenyl]benzoate;
ethyl p-[(E)-2-(6,7,8,9-tetrahydro-5,5,9-trimethyl-5H-benzocycloheptene-2-yl)propenyl]benzoate;
ethyl p-[(E)-2-(6,7,8,9-tetrahydro-5,9,9-tetramethyl-5H-benzocycloheptene-2-yl)propenyl]benzoate;
ethyl p-[(E)-2-(6,7,8,9-tetrahydro-7,7,9-trimethyl-5H-benzocycloheptene-2-yl)propenyl]benzoate:
methyl p-[(E)-2-(6,7,8,9-tetrahydro-7,7,9,9-tetramethyl-5H-benzocycloheptene-2-yl)propenyl]benzoate;
ethyl p-[(E)-2-(7-ethyl-6,7,8,9-tetrahydro-7-methyl-5H-benzocycloheptene-2-yl)propenyl]benzoate;
p-[(E)-2-(6,7,8,9-tetrahydro-5H-benzocyclohepten-2-yl)propenyl]benzoic acid;
p-[(E)-2-(6,7,8,9-tetrahydro-7,7-dimethyl-5H-benzocyclohepten-2-yl)propenyl]benzoic acid;
p-[(E)-2-(6,7,8,9-tetrahydro-5,5 9,9-tetramethyl-5H-benzocycloheptene-2-yl)propenyl]benzoic acid;
ethyl p-[(E)-2-(6,7,8,9-tetrahydro-7-methyl-5H-benzocycloheptene-2-yl)propenyl]benzoate;
p-[(E)-2-(6,7,8,9-tetrahydro-6,6,8,8-tetramethyl-5H-benzocycloheptene-2-yl)propenyl]benzoic acid;
methyl p-[(E)-(6,7,8,9 tetrahydro-3,7,7-trimethyl-5H-benzocycloheptene-2-yl)propenyl]benzoate;
ethyl p-[(E)-2-(6,7,8,9-tetrahydro-9-methyl-5H-benzocycloheptene-2-yl)propenyl]benzoate;
p-[(E)-2-(6,7,8,9-tetrahydro-7,7,9,9-tetramethyl-5H-benzocycloheptene-2-yl)propenyl]benzoic acid;
p-[(Z)-(6,7,8,9-tetrahydro-7,7-dimethyl-3-octyl-5H-benzocycloheptene-2-yl)propenyl]benzoic acid;
p-[(Z)-2-(3-bromo-6,7,8,9-tetrahydro-7 7-dimethyl-5H-benzocycloheptene-2-yl)propenyl]benzoic acid;
p-[(Z)-2-(6,7,8,9-tetrahydro-3,7,7-trimethyl-5H-benzocyclohepten-2-yl)propenyl]benzoic acid and
ethyl p-[(E)-2-(6,7,8,9-tetrahydro-5H-benzocyclo-hepten-2-yl)propenyl]benzoate.

12. A compound in accordance with claim 1, selected from the group consisting of ethyl p-[(E)-2-[5,6,8,9-tetrahydrospiro [7H-benzocyclohepten-7,1'-cyclopropane]-2-yl] propenyl]benzoate and ethyl p-[(E)-2-[5,6,8,9-tetrahydrospiro[7H-benzocyclohepten-7,1'-cyclopentane]-2-yl]propenyl]benzoate.

13. A compound in accordance with claim 1, selected from the group consisting of methyl p-[(E)-2-(6,7,8,9-tetrahydro-7-oxo-5H-benzocyclohepten-2-yl)propenyl]benzoate and
ethyl p-[(E)-2-(6,7,8,9-tetrahydro-6,6,8,8-tetramethyl-7-oxo-5H-benzocyclohepten-2-yl)propenyl]benzoate.

14. A compound in accordance with claim 1, selected from the group consisting of ethyl p-[(E)-2-(6,7,8,9-tetrahydro-10-acetoxy-5,9-dimethyl-5,9-methano-5H-benzocyclohepten-2-yl)propenyl]-benzoate; p0 p-[(E)-2-(6,7,8,9-tetrahydro-10-hydroxy-5,9-dimethyl-5,9-methano-5H-benzocyclohepten-2-yl)propenyl]benzoic acid;
ethyl p-[(E)-2-(6,7,8,9-tetrahydro-5,9-dimethyl-5,9-methano-5H-benzocyclohepten-2-yl)propenyl]benzoate and p0 p-[(E)-2-(6,7,8,9-tetrahydro-5,9-dimethyl-5,9-methano-5H-benzocyclohepten-2-yl)propenyl]benzoic acid.

15. A pharmaceutical composition comprising an effective amount of a compound of the formula

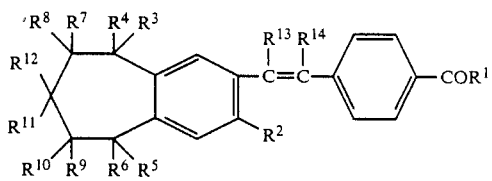

wherein
$R^1$ is hydroxy, lower-alkoxy, amino, mono- or di-lower-alkylamino;
$R^2$ is hydrogen, alkyl, alkoxy or halogen;
$R^3$, $R^4$, $R^5$, $R^6$, and independently are hydrogen or lower-alkyl;
$R^3$ and $R^5$ taken together are methylene or hydroxymethylene;
$R^7$, $R^9$ and $R^{10}$ independently are hydrogen or lower-alkyl;
$R^{11}$ and $R^{12}$ taken together are oxo or spiro-cyclo-lower alkyl; or $R^{11}$ is hydrogen and $R^{12}$ is hydroxy or acetoxy; and one of the residues $R^{13}$ and $R^{14}$ is hydrogen and the other is lower-alkyl or trifluoromethyl, or, when $R^1$ is hyohoxy, a physiologically compatible salts, and an inert carrier thereof.

16. A pharmaceutical composition in accordance with claim 15, wherein $R^1$ is hydroxy, lower-alkoxy, amino, mono- or di-lower-alkyl-amino; $R^2$ is hydrogen, alkyl, alkoxy or halogen; $R^3$, $R^4$, $R^5$, $R^6$, $R^{11}$ and $R^{12}$ independently are hydrogen or lower-alkyl; $R^3$ and $R^5$ taken together are methylene; $R^7$, $R^8$, $R^9$ and $R^{10}$ independently are hydrogen or lower-alkyl; $R^{11}$ and $R^{12}$ taken together are oxo or $R^{11}$ is hydrogen and $R^{12}$ is hydroxy; and one of the residues and $R^{13}$ and $R^{14}$ is hydrogen and the other is lower-alkyl or trifluoromethyl.

17. A pharmaceutical composition in accordance with claim 16, wherein the compound of formula I is ethyl p-[(E)-2-(6,7,8,9-tetrahydro-7,7-dimethyl-5H-benzocyclo-hepten-2-yl)propenyl]benzoate.

18. A pharmaceutical composition in accordance with claim 16, wherein the compound of formula I is selected from the group consisting of ethyl p-[(E)-2-

(6,7,8,9-tetrahydro-9,9-dimethyl-5H-benzocyclo-hept-en-2-yl)propenyl]benzoate;
ethyl p-[(E)-2-(6,7,8,9-tetrahydro-5,5-dimethyl-5H-benzocycloheptene-2-yl)propenyl]benzoate;
ethyl p-[(E)-2-(6,7,8.9-tetrahydro-5,9,9-trimethyl-5H-benzocycloheptene-2-yl)propenyl]benzoate;
ethyl p-[(E)-2-(6,7,8.9-tetrahydro-5,5,9-trimethyl-5H-benzocycloheptene-2-yl)propenyl]benzoate;
ethyl p-[(E)-2-(6,7,8,9-tetrahydro-5,5,9,9-tetramethyl-5H-benzocyclohepten-2-yl)propenyl]benzoate;
ethyl p-[(E)-2-(6,7,8,9-tetrahydro-7,7,9-trimethyl-5H-benzocycloheptene-2-yl)propenyl]benzoate;
methyl p-[(E)-2-(6,7,8,9-tetrahydro-7,7,9,9-tetramethyl-5H-benzocyclohepten-2-yl)propenyl]benzoate;
ethyl p-[(E)-2-(7-ethyl-6,7,8,9-tetrahydro-7-methyl-5H-benzocyclohepten-2-yl)propenyl]benzoate;
p-[(E)-2-(6,7,8,9-tetrahydro-5H-benzocyclohepten-2-yl)propenyl]benzoic acid;
p-[(E)-2-(6,7,8,9-tetrahydro-7,7-dimethyl-5H-benzocyclohepten-2-yl)propenyl]benzoic acid;
p-[(E)-2-(6,7,8,9-tetrahydro-5,5,9,9-tetramethyl-5H-benzocycloheptene-2-yl)propenyl]benzoic acid;
ethyl p-[(E)-2-(6,7,8,9-tetrahydro-7-methyl-5H-benzocyclohepten-2-yl)propenyl]benzoate;
p-[(E)-2-(6,7,8,9-terrahydro-6,6,8,8-tetramethyl-5H-benzocyclohepten-2-yl)propenyl]benzoic acid;
methyl p-[(E)-(6,7,8.9-tetrahydro-3,7,7-trimethyl-5H-benzocyclohepten-2-yl)propenyl]benzoate;
ethyl p-[(E)-2-(6,7,9-tetrahydro-9-methyl-5H-benzocyclohepten-2-yl)propenyl]benzoate;
p-[(E)-2-(6,7,8,9-terrahydro-7,7,9,9-tetramethyl-5H-benzocyclohepten-2-yl)propenyl]benzoic acid;
p-[(Z)-(6,7,8,9-tetrahydro-7,7-dimethyl-3-octyl-5H-benzocycloheptene-2-yl)propenyl]benzoic acid;
p-(Z)-2-(3-bromo-6,7-8,9-tetrahydro-7,7-dimethyl-5H-benzocycloheptene-2-yl)propenyl]benzoic acid;
p-[(Z)-2-(6,7,8,9-tetrahydro-3,7,7-trimethyl-5H-benzocyclohepten-2-yl)propenyl]benzoic acid and
ethyl p-[(E)-2-(6,7,8,9-tetrahydro-5H-benzocyclohepten-2-yl)propenyl]benzoate.

19. A method of administering to a host requiring an anti-seborrheic, anti-keratinizing, anti-neoplastic and anti-allergic or anti-inflammatory agent, an effective amount of a compound of the formula

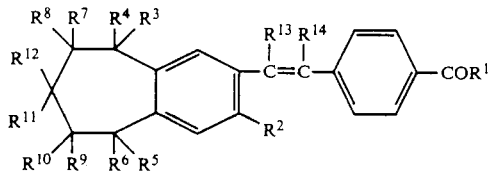

wherein
$R^1$ is hydroxy, lower-alkoxy, amino, mono- or di-lower-alkylamino;
$R^2$ is hydrogen, alkyl, alkoxy or halogen;
$R^3$, $R^4$, $R^5$, $R^6$, $R^{11}$ and $R^{12}$ independently are hydrogen or lower-alkyl;
$R^3$ and $R^5$ taken together are methylene or hydroxymethylene;
$R^7$, $R^8$, $R^9$ and $R^{10}$ independently are hydrogen or lower-alkyl;

$R^{11}$ and $R^{12}$ taken together are oxo or spiro-cyclo-lower alkyl; or $R^{11}$ is hydrogen and
$R^{12}$ is hydroxy or acetoxy; and one of the residues $R^{13}$ and $R^{14}$ is hydrogen and the other is lower-alkyl or trifluoromethyl, or when $R^1$ is hyohoxy, a physiologically compatible salt thereof.

20. A method in accordance with claim 19, wherein $R^1$ is hydroxy, lower-alkoxy, amino, mono or di-lower alkyl-amino; $R^2$ is hydrogen, alkyl, alkoxy or halogen; $R^3$, $R^4$, $R^5$, $R^6$, and independently are hydrogen or lower-alkyl; $R^3$ and $R^5$ taken together are methylene; $R^7$, $R^9$ and independently are hydrogen or lower-alkyl; taken together are oxo or is hydrogen and is hydroxy; and one of the residues $R^{13}$ and hydrogen and the other is lower-alkyl or trifluoromethyl.

21. A method in accordance with claim 21, wherein the compound of formula I is ethyl p-[(E)-2-(6,7,8,9-tetrahydro-7,7-dimethyl-5H-benzocyclohepten-2-yl)propenyl]benzoate.

22. A method in accordance with claim 20, wherein the compound formula I is selected from the group consisting of ethyl p-[(E)-2-(6,7,8,9-tetrahydro-9,9-dimethyl-5H-benzocyclohepten-2-yl)propenyl]benzoate;
ethyl p-[(E)-2-(6,7,8,9-tetrahydro-5,5-dimethyl-5H-benzocycloheptene-2-yl)propenyl]benzoate;
ethyl p-[(E)-2-(6,7,8,9-tetrahydro-5,9,9-trimethyl-5H-benzocycloheptene-2-yl)propenyl]benzoate;
ethyl p-[(E)-2-(6,7,8,9-tetrahydro-5,5,9-trimethyl-5H-benzocycloheptene-2-yl)propenyl]benzoate;
ethyl p-[(E)-2-(6,7,8,9-tetrahydro-5,5,9,9-tetramethyl-5H-benzocyclohepten-2-yl)propenyl]benzoate;
ethyl p-[(E)-2-(6,7,8,9-tetrahydro-7,7,9-trimethyl-5H-benzocyclohepten-2-yl)propenyl]benzoate;
methyl p-[(E)-2-(6,7,8,9-tetrahydro-7,7,9,9-tetramethyl-5H-benzocyclohepten-2-yl)propenyl]benzoate;
ethyl p-[(E)-2-(7-ethyl-6,7,8,9-tetrahydro-7-methyl-5H-benzocyclohepten-2-yl)propenyl]benzoate;
p-[(E)-2-(6,7,8,9-tetrahydro-5H-benzocyclohepten-2-yl)propenyl]benzoic acid;
p-[(E)-2-(6,7,8,9-tetrahydro-7,7-dimethyl-5H-benzocyclohepten-2-yl)propenyl]benzoic acid;
p-[(E)-2-(6,7,8,9-tetrahydro-5,5,9,9-tetramethyl-5H-benzocycloheptene-2-yl)propenyl]benzoic acid;
ethyl p-[(E)-2-(6,7,8,9-tetrahydro-7-methyl-5H-benzocyclohepten-2-yl)propenyl]benzoate;
p-[(E)-2-(6,7,8,9-terrahydro-6,6,8,8-tetramethyl-5H-benzocyclohepten-2-yl)propenyl]benzoic acid;
methyl p-[(E)-(6,7,8.9-tetrahydro-3,7,7-trimethyl-5H-benzocycloheptene-2-yl)propenyl]benzoate;
ethyl p-[(E)-2-(6,7,9-tetrahydro-9-methyl-5H-benzocyclohepten-2-yl)propenyl]benzoate;
p-[(E)-2-(6,7,8,9-terrahydro-7,7,9,9-tetramethyl-5H-benzocycloheptene-2-yl)propenyl]benzoic acid;
p-[(Z)-(6,7,8,9-tetrahydro-7,7-dimethyl-3-octyl-5H-benzocycloheptene-2-yl)propenyl]benzoic acid;
p-(Z)-2-(3-bromo-6,7-8,9-tetrahydro-7,7-dimethyl-5H-benzocycloheptene-2-yl)propenyl]benzoic acid;
p-[(Z)-2-(6,7,8,9-tetrahydro-3,7,7-trimethyl-5H-benzocyclohepten-2-yl)propenyl]benzoic acid and
ethyl p-[(E)-2-(6,7,8,9-tetrahydro-5H-benzocyclohepten-2-yl)propenyl]benzoate.

* * * * *

UNITED STATES PATENT AND TRADEMARK OFFICE
CERTIFICATE OF CORRECTION

PATENT NO. : 4,992,574

DATED : February 12, 1991

INVENTOR(S) : Klaus et al.

It is certified that error appears in the above-identified patent and that said Letters Patent is hereby corrected as shown below:

Claim 1, Column 16, line 54,
"$R^7, R^9$" should be --- $R^7, R^8, R^9$ ---

Claim 11, Column 17, line 33,
"5,9,9" should be --- 5,5,9,9 ---

Claim 14, Column 18, line 13,
delete p0    (PTO)

Claim 14, Column 18, line 19,
delete p0    (PTO)

Claim 15, Column 18, line 38,
"$R^3, R^4, R^5, R^6$ and" should be ---$R^3, R^4, R^5, R^6, R^{11}$ and $R^{12}$ ---

Claim 15, Column 18, line 42,
"$R^7, R^9$ and $R^{10}$" should be ---$R^7, R^8, R^9$ and $R^{10}$---

Claim 15, Column 18, line 49,
"hyohoxy" should be --- hydroxy ---

Claim 18, Column 19, line 29,
"(6,7,9" should be ---(6,7,8,9 ---

Claim 19, Column 20, line 5,
"hyohoxy" should be --- hydroxy ---

Claim 20, Column 20, line 10,
"$R^3, R^4, R^5, R^6$ and" should be --- $R^3, R^4, R^5, R^6, R^{11}$ and $R^{12}$ ---

Claim 20, Column 20, line 12,
"$R^7, R^9$ and" should be ---$R^7, R^8, R^9$ and $R^{10}$ ---   (PTO)

Claim 20, Column 20, line 13,
"taken together" should be --- $R^{11}$ and $R^{12}$ taken together ---

Claim 20, Column 20, line 13,
"or is hydrogen" should be --- or $R^{11}$ is hydrogen ---

UNITED STATES PATENT AND TRADEMARK OFFICE
CERTIFICATE OF CORRECTION

PATENT NO. : 4,992,574

DATED : February 12, 1991

INVENTOR(S) : Klaus et al.

It is certified that error appears in the above-identified patent and that said Letters Patent is hereby corrected as shown below:

Claim 20, Column 20, line 13,
"and is hydroxy" should be --- and $R^{12}$ is hydroxy ---

Claim 20, Column 20, line 14,
"$R^{13}$ and hydrogen" should be --- $R^{13}$ and $R^{14}$ is hydrogen ---

Claim 22, Column 20, line 51,
"(6,7,9" should be ---(6,7,8,9 ---

Signed and Sealed this

Twentieth Day of October, 1992

*Attest:*

DOUGLAS B. COMER

*Attesting Officer*       *Acting Commissioner of Patents and Trademarks*